US012734402B2

(12) United States Patent
Zeng et al.

(10) Patent No.: US 12,734,402 B2
(45) Date of Patent: Sep. 15, 2026

(54) WRIST REHABILITATION TRAINING SYSTEM BASED ON MUSCLE COORDINATION AND VARIABLE STIFFNESS IMPEDANCE CONTROL

(71) Applicant: SOUTHEAST UNIVERSITY, Nanjing (CN)

(72) Inventors: Hong Zeng, Nanjing (CN); Yinxin Duan, Nanjing (CN); Xiao Li, Nanjing (CN); Qingqing Chen, Nanjing (CN); Aiguo Song, Nanjing (CN)

(73) Assignee: SOUTHEAST UNIVERSITY, Nanjing (CN)

( * ) Notice: Subject to any disclaimer, the term of this patent is extended or adjusted under 35 U.S.C. 154(b) by 660 days.

(21) Appl. No.: 18/138,154

(22) Filed: Apr. 24, 2023

(65) Prior Publication Data

US 2023/0256296 A1 Aug. 17, 2023

Related U.S. Application Data

(63) Continuation of application No. PCT/CN2022/107560, filed on Jul. 25, 2022.

(30) Foreign Application Priority Data

Apr. 26, 2022 (CN) ........................ 202210443610.3

(51) Int. Cl.

*A63B 23/14* (2006.01)
*A61B 5/397* (2021.01)
*A63F 13/212* (2014.01)

(52) U.S. Cl.

CPC .............. *A63B 23/14* (2013.01); *A61B 5/397* (2021.01); *A63F 13/212* (2014.09); *A61B 2505/09* (2013.01)

(58) Field of Classification Search

CPC ....... A63B 23/14; A63F 13/212; A61B 5/397; A61B 2505/09

See application file for complete search history.

(56) References Cited

U.S. PATENT DOCUMENTS

2016/0066836 A1* 3/2016 Schneider ............ A61B 5/0004 600/546
2016/0096073 A1* 4/2016 Rahman .................. G06F 3/011 463/7
2017/0209737 A1* 7/2017 Tadi ...................... A61B 5/0036
2020/0170547 A1* 6/2020 Bai ....................... A61B 5/1107

* cited by examiner

*Primary Examiner* — Marshall L Werner
(74) *Attorney, Agent, or Firm* — JCIPRNET

(57) ABSTRACT

A wrist rehabilitation training system based on muscle coordination and variable stiffness impedance control includes the following modules: an electromyographic signal collection and preprocessing module, a muscle co-decomposition and mapping model obtaining module, a man-machine interactive control module, and a virtual reality serious game module; collects a surface electromyographic signal of a forearm of a user, obtains time-domain coordination through non-negative matrix factorization, establishes a position and stiffness estimation model, and controls motion of a target in a serious game through variable stiffness impedance control, so as to complete a training task.

4 Claims, 1 Drawing Sheet

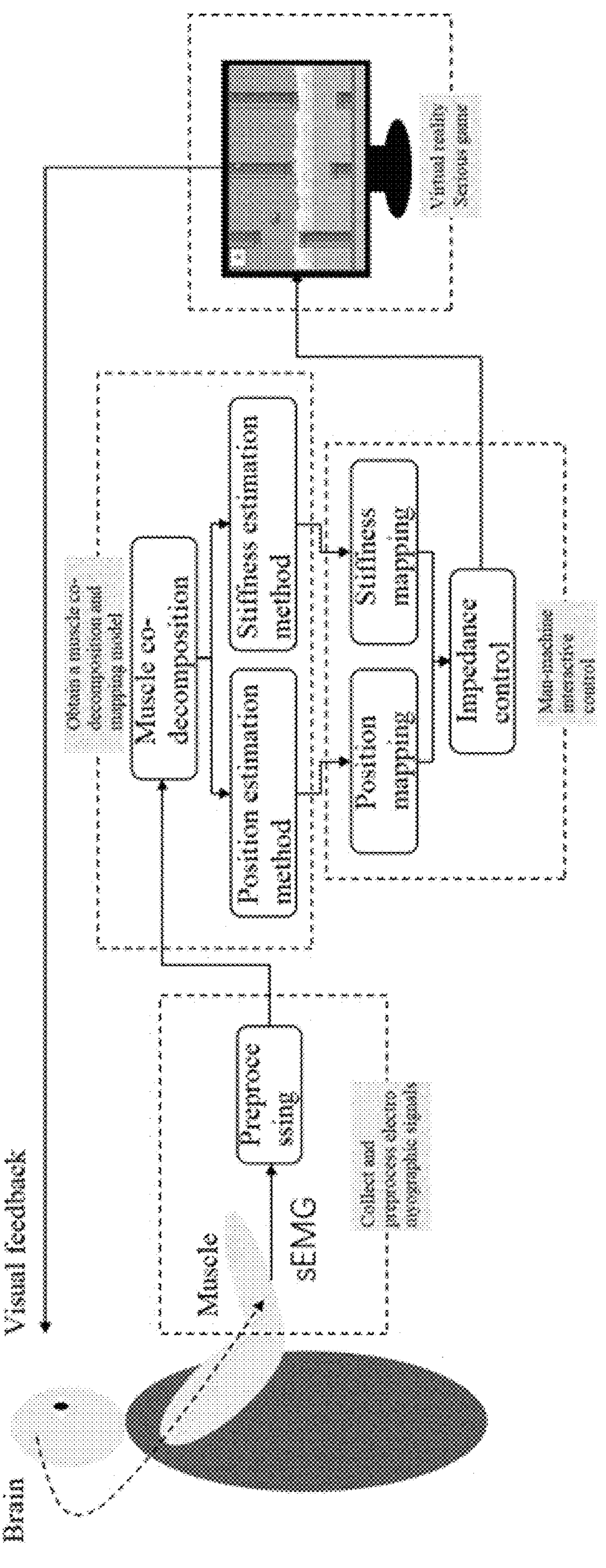
Brain
Visual feedback
Muscle
sEMG
Preproce ssing
Collect and preprocess electro myographic signals
Muscle co-decomposition
Obtain a muscle co-decomposition and mapping model
Position estimation method
Stiffness estimation method
Position mapping
Stiffness mapping
Impedance control
Man-machine interactive control
Virtual reality Serious game

WRIST REHABILITATION TRAINING SYSTEM BASED ON MUSCLE COORDINATION AND VARIABLE STIFFNESS IMPEDANCE CONTROL

CROSS-REFERENCE TO RELATED APPLICATIONS

This application is the U.S. continuation application of International Application No. PCT/CN2022/107560 filed on 25 Jul. 2022 which designated the U.S. and claims priority to Chinese Application No. CN202210443610.3 filed on 26 Apr. 2022, the entire contents of each of which are hereby incorporated by reference.

TECHNICAL FIELD

The present invention belongs to the fields of rehabilitation training and motion learning, and particularly relates to a wrist rehabilitation training system based on muscle coordination and variable stiffness impedance control.

BACKGROUND ART

Stroke, an acute cerebrovascular disease, causes brain tissue damage due to sudden rupture or blockage of blood vessels in a brain and further inability of blood to flow into the brain. "China Stroke Prevention Report 2019" outlines that stroke is a major chronic disease that seriously harms health of Chinese citizens. The stroke is high in incidence and disability rates. 70%-80% of patients of the stroke are likely to have hemiplegia symptoms and lose an ability to live independently, which not only seriously influences their living standards but can cause various physical and psychological diseases and even endanger their lives. With accelerating aging and urbanization of population and unhealthy lifestyles of residents, an increasing prevalence rate of stroke has brought a serious burden to families and society.

At present, plasticity of a human central nervous system has been verified. Scientific and regular rehabilitation training can assist patients to improve their damaged functions and recover their limb functions. For recovery of motion functions, stroke patients generally undergo rehabilitation training with long-time guidance and assistance of the professional medical staff. However, a serious imbalance between the number of patients and the number of medical staff leads to untimely rehabilitation training of many patients, and further influences recovery effect and opportunity of patients. Limbs of patients are driven to be treated mainly by the medical staff or simple machines through traditional rehabilitation training methods, so training intensity and time can be hardly ensured. In recent years, the sensor technology, man-machine interface technology, virtual reality technology and robot technology have been developed rapidly to overcome defects of traditional rehabilitation training. A more accurate and intelligent method can be provided for rehabilitation training. An exoskeleton device and a robot use motion signals (such as position signals, force signals and mixed force potential signals) or physiological signals (electromyographic signals, electroencephalographic signals and electro-oculographic signals) of human bodies as interactive information, and conduct rehabilitation training on limbs of patients through various control algorithms. Relevant information in a training process can be recorded for analysis by professional therapists, such that a rehabilitation training method can be adjusted in time.

A surface electromyographic signal is a bioelectric signal generated through muscle contraction control by a nerve center. It is often used as an interactive signal of various rehabilitation training systems because it contains action information ahead of corresponding actions of a human body and can better reflect human action intentions. A neuromuscular coordinative control theory describes a process from a central nervous system to muscles. The central nervous system generates a small number of signals. These signals are assigned to the corresponding muscles via a network, and the muscles contract to generate forces, so as to move limbs. Therefore, electromyographic signals are converted into motion signals in rehabilitation training through muscle coordination.

As the most flexible part of a human body, a hand has the greatest influence on people's daily lives and is also the most vulnerable part. Most stroke patients tend to have abnormal hand muscle force symptoms and hand dysfunction. It is very important to recover of hand functions of patients. Demands of hand rehabilitation training are diverse, so rehabilitation difficulty is high. At present, passive rehabilitation training is mostly used, in which patients are driven to complete preset tracks by robots, and initiative and enthusiasm of patients cannot play an important role. In addition, most rehabilitation training only focuses on recovery of wrist actions of patients, instead of recovery of hand muscle force. During interaction with a physical environment, it is necessary to effectively change muscle strength, so as to improve stability and accuracy during interaction with an environment.

SUMMARY

In order to solve the above problems, the present invention discloses a wrist rehabilitation training system based on muscle coordination and variable stiffness impedance control, which extracts joint angle and stiffness information from surface electromyographic signals and applies the information to rehabilitation training games, such that a subject may complete the training games so as to achieve a rehabilitation training effect on wrists.

In order to achieve the above objective, the present invention uses the following technical solution:

The wrist rehabilitation training system based on muscle coordination and variable stiffness impedance control includes:

- an electromyographic signal collection and preprocessing module configured to collect and filter surface electromyographic signals during motion by means of a surface electromyographic signal sensor;
- a muscle co-decomposition and mapping model obtaining module configured to establish a surface electromyographic signal and joint angle mapping model and a surface electromyographic signal and human stiffness mapping model through a muscle co-decomposition method and a regression network model;
- a man-machine interactive control module configured to control an agent in a virtual environment through an impedance control method, where stiffness in impedance control changes with stiffness of a human arm; and
- a virtual reality serious game module configured to generate serious game difficulty and virtual interference suitable for rehabilitation training of a user and provide visual feedback.

Furthermore, the electromyographic signal collection and preprocessing module is configured to:

collect the surface electromyographic signals, specifically, use Delsys to collect surface electromyographic signals of a flexor carpi radialis muscle, an extensor carpi radialis muscle, a flexor carpi ulnaris muscle, an extensor carpi ulnaris muscle, a flexor digitorum muscle and an extensor digitorum muscle of a human body; and preprocess the surface electromyographic signals, where a processing method includes five steps of full-wave rectification, low-pass filtering, normalization, nerve activation model extraction, and muscle activation model extraction.

Furthermore, the muscle co-decomposition and mapping model obtaining module is configured to:

conduct muscle co-decomposition, specifically, conduct a non-negative matrix factorization method on a preprocessed signal, so as to obtain space-domain coordination and space-domain coordination, where the non-negative matrix factorization method is as follows:

$$Z(t)=W\cdot C(t)$$

where Z(t) is a preprocessed surface electromyographic signal, W is space-domain coordination, C(t) is space-domain coordination, and all elements in the non-negative matrix factorization method are non-negative;

obtain a joint angle mapping model, specifically, train a multi-layer perception model by using time-domain coordinative data and motion tag data, so as to obtain the joint angle mapping model:

$$x(t)=\mathrm{MLP}(W^{+}\cdot Z(t))$$

where x(t) is a joint angle, $W^{+}$ is an inverse matrix of time-domain coordination, Z(t) is the preprocessed surface electromyographic signal, and MLP(·) is a trained multi-layer perception model; and obtain a human stiffness mapping model, specifically, use a coordination effect model to project the preprocessed surface electromyographic signal to coordination effects with different freedom degrees and different directions, where the coordination effects are contributions of muscle contraction in all directions, and further obtain, according to a co-contraction principle, a model of the surface electromyographic signal to human stiffness:

$$K_i(t)=\min(W_{i+}^{T}\cdot Z(t),W_{i-}^{T}Z(t))$$

where $K_i(t)$ is a stiffness value of each freedom degree, $W_{i+}^{T}$ and $W_{i-}^{T}$ are coordination effect coefficient matrices in two directions of the freedom degree, and Z(t) is the preprocessed surface electromyographic signal.

Furthermore, the man-machine interactive control module uses a variable stiffness impedance control method to control the agent in the virtual environment, virtual impedance control involves a damping-spring-mass system, and an expression method of the system is:

$$M\ddot{x}(t)+B\dot{x}(t)+Kx(t)=F_{ext}$$

where M is an object mass, B is a damping coefficient, K is a spring (stiffness) coefficient, x(t), $\dot{x}(t)$ and $\ddot{x}(t)$ are a current position, a current speed and a current acceleration, respectively, and $F_{ext}$ is an extra interference force. In the method, x(t) may be obtained according to a surface electromyographic signal and joint angle relationship model, and $\dot{x}(t)$ and $\ddot{x}(t)$ are a first-order derivative and a second-order derivative of x(t), respectively; and K may be obtained according to the model of the surface electromyographic signal to the human stiffness, a relationship between the damping coefficient and the spring (stiffness) coefficient of the system is $B=2\sqrt{K}$, the object mass M is a mass of a target preset in a training game, and the extra interference force $F_{ext}$ is a variable virtual force set in the training game.

Furthermore, the virtual reality serious game module includes:

a serious game generation module configured to generate different rehabilitation training serious games in different training stages on the basis of a pygame platform;

a feedback module configured to provide a patient with game information such as interference in the virtual environment and a motion position of a virtual agent; and a serious game adjustment module configured to adjust the serious game difficulty according to an effect of each cycle of rehabilitation training, so as to increase challenges of rehabilitation training.

The present invention has the beneficial effects:

(1) The system uses a muscle coordination method for estimating a joint angle, more intuitively reflects a relationship between joint motion and the human stiffness and muscle activation, and achieves more accurate mapping from the electromyographic signals to the joint angle and stiffness.

(2) The system uses a virtual impedance control method and applies a virtual force in a virtual scene, such that muscle force may be directly trained, and more efficient rehabilitation training may be achieved.

(3) The rehabilitation training system adjusts the training game scene and complexity according to training performance of the subject, such that rehabilitation training may be more interesting, and a rehabilitation training effect may be effectively improved.

BRIEF DESCRIPTION OF THE DRAWINGS

FIGURE is a block diagram of a system of the present invention.

DETAILED DESCRIPTION OF THE EMBODIMENTS

The present invention will be further described with reference to the accompanying drawings and specific embodiments. It should be understood that the following specific embodiments are only used to illustrate the present invention and are not used to limit the scope of the present invention.

A rehabilitation training task in the present invention generally refers to free motion of wrists and fingers in daily lives, such as taking things, doing housework or other complex tasks. Herein, a therapist/technician informs a subject of a game target, and the subject may control a target to move through actions of fingers and wrists, so as to complete the task.

As shown in FIGURE, a wrist rehabilitation training system based on muscle coordination and variable stiffness impedance control according to an example of the present invention is used through the following steps:

(1) Surface electromyographic signals during flexion and extension of wrists and fingers are collected and preprocessed.

The surface electromyographic signals are interactive information most commonly used in the rehabilitation training system. The surface electromyographic signals contain a large amount of action and stiffness information, and the information may be decomposed through specific algorithms and used to control an artificial limb, a robot, or a target in a virtual scene. A Delsys wireless surface electromyographic collection system is used to collect bioelectric signals generated during muscle motion, a subject needs to conduct flexion and extension of wrists and fingers separately, and surface electromyographic signals of a flexor carpi radialis muscle, an extensor carpi radialis muscle, a flexor carpi ulnaris muscle, an extensor carpi ulnaris muscle, a flexor digitorum muscle and an extensor digitorum muscle are recorded. Operations such as full-wave rectification and low-pass filtering are conducted on the collected surface electromyographic signals, so as to obtain an envelope curve of the electromyographic signals, then normalization is conducted such that processed data is within a range of 0-1, then a nerve activation degree is obtained through a nerve activation model, and finally a muscle activation degree is obtained through a muscle activation model.

(2) A surface electromyographic signal and joint angle relationship model is determined.

According to a muscle co-decomposition principle, the preprocessed electromyographic signals are decomposed through a non-negative matrix factorization method. Muscle co-decomposition is conducted on signals generated during flexion and extension of wrists and fingers separately.

$$Z_{wf}(t)=W_{wf}\cdot C_{wf}(t)$$

$$Z_{we}(t)=W_{we}\cdot C_{we}(t)$$

$$Z_{ff}(t)=W_{ff}\cdot C_{ff}(t)$$

$$Z_{fe}(t)=W_{fe}\cdot C_{fe}(t)$$

$Z_{wf}(t)$, $Z_{we}(t)$, $Z_{ff}(t)$ and $Z_{fe}(t)$ are electromyographic signals during wrist flexion, wrist extension, finger flexion and finger extension, respectively, $W_{wf}$, $W_{we}$, $W_{ff}$ and $W_{fe}$ are space-domain coordination effects corresponding to wrist flexion, wrist extension, finger flexion and finger extension, respectively, and $C_{wf}(t)$, $C_{we}(t)$, $C_{ff}(t)$ and $C_{fe}(t)$ are time-domain coordination effects corresponding to wrist flexion, wrist extension, finger flexion and finger extension, respectively. The obtained space-domain coordination effects are combined in columns, so as to obtain overall space-domain coordination:

$$W=[W_{wf},W_{we},W_{ff},W_{fe}]$$

A multi-layer perception model regression network is trained by using obtained time-domain coordination and tag data, so as to obtain a relationship module of an electromyographic signal to a joint angle:

$$x(t)=\mathrm{MLP}(W^{+}\cdot Z(t))$$

where $x(t)$ is a joint angle, $W^{+}$ is an inverse matrix of time-domain coordination, $Z(t)$ is the preprocessed surface electromyographic signal, and $\mathrm{MLP}(\cdot)$ is a trained multi-layer perception model.

(3) A surface electromyographic signal and human stiffness model is determined.

The preprocessed surface electromyographic signal is projected to coordination effects with different freedom degrees and different directions according to a coordination effect model, where the coordination effects are contributions of muscle contraction in all directions, and a specific projection method is the same as the muscle co-decomposition method in (2). According to a co-contraction principle, a model of a surface electromyographic signal to human stiffness is obtained as follows:

$$K_w(t)=\min(W_{wf}^{T}\cdot Z(t),W_{we}^{T}\cdot Z(t))$$

$$K_f(t)=\min(W_{ff}^{T}\cdot Z(t),W_{fe}^{T}\cdot Z(t))$$

where $K_w(t)$ and $K_f(t)$ are stiffness in a wrist flexion and extension direction and stiffness in a finger flexion and extension direction, respectively $W_{wf}^{T}$, $W_{we}^{T}$, $W_{ff}^{T}$ and $W_{fe}^{T}$ are coordination effect coefficient matrices in wrist flexion, wrist extension and finger flexion directions, respectively, and $Z(t)$ is the preprocessed surface electromyographic signal.

(4) A task control scene is initialized and task complexity is set.

In order to improve enthusiasm of a subject in participating in rehabilitation training, two games, flying bird and captain rogers, are used in different training game scenes, and the game complexity is changed by increasing or decreasing obstacles in the game.

(5) Rehabilitation training is conducted.

Through multi-time long-term training, the subject may undergo effective rehabilitation. A virtual impedance control method is used in control:

$$M\ddot{x}(t)+B\dot{X}(t)+Kx(t)=F_{ext}$$

where M is an object mass, B is a damping coefficient, K is a spring (stiffness) coefficient, $x(t)$, $\dot{x}(t)$ and $\ddot{x}(t)$ are a current position, a current speed and a current acceleration, respectively, and $F_{ext}$ is an extra interference force. A joint angle obtained according to the surface electromyographic signal and joint angle relationship model is mapped to coordinates of a control target of a training game through projection transformation. Human stiffness obtained according to the surface electromyographic signal and human stiffness model is taken as the spring (stiffness) coefficient of the virtual impedance control method. The subject needs to control actual output targets so as to complete related tasks.

(6) The task scene and task complexity are adjusted according to game performance.

During rehabilitation training, time and a score of each task completed by the subject may be recorded. The task scene and task complexity are adjusted according to the performance after each cycle of training. If the time to complete the game decreases or the score increases, the game difficulty is increased, and otherwise, the game difficulty is decreased.

It should be noted that the above description only illustrates the technical idea of the present invention, and cannot be used to limit the protection scope of the present invention. Those of ordinary skill in the art can also make some improvements and modifications without departing from the principle of the present invention, and these improvements and modifications should also fall within the protection scope of claims of the present invention.

What is claimed is:

1. A wrist rehabilitation training system based on muscle coordination and variable stiffness impedance control, comprising:

an electromyographic signal collection and preprocessing module, comprising a surface electromyographic signal sensor, wherein the surface electromyographic signal sensor is configured to collect surface electromyographic signals and the electromyographic signal collection and preprocessing module preprocess the surface electromyographic signals;

a processor; and a memory storing instructions that, when executed by the processor, cause the processor to perform steps comprises:

decomposing the preprocessed surface electromyographic signals through a non-negative matrix factorization method and to train a multi-layer perception model regression network to establish a surface electromyographic signal and joint angle mapping model and a surface electromyographic signal and human stiffness mapping model;

controlling an agent in a virtual environment; and generating a virtual reality game configured to generate game difficulty and virtual interference suitable for rehabilitation training of a user and provide visual feedback.

2. The wrist rehabilitation training system based on muscle coordination and variable stiffness impedance control according to claim 1, wherein the electromyographic signal collection and preprocessing module comprises:

a Delsys wireless surface electromyographic collection device, configured to collect surface electromyographic signals of a flexor carpi radialis muscle, an extensor carpi radialis muscle, a flexor carpi ulnaris muscle, an extensor carpi ulnaris muscle, a flexor digitorum muscle and an extensor digitorum muscle of a human body, the electromyographic signal collection and preprocessing module is configured to preprocess the surface electromyographic signals through full-wave rectification, low-pass filtering, normalization, nerve activation degree extraction, and muscle activation degree extraction.

3. The wrist rehabilitation training system based on muscle coordination and variable stiffness impedance control according to claim 1, wherein the processor uses a variable stiffness impedance control method to control the agent in the virtual environment, virtual impedance control involves a damping-spring-mass system, and an expression method of the system is:

$$M\ddot{x}(t)+B\dot{x}(t)+Kx(t)=F_{ext}$$

wherein M is an object mass, B is a damping coefficient, K is a spring (stiffness) coefficient, x(t), $\dot{x}$(t) and $\ddot{x}$(t) are a current position, a current speed and a current acceleration, respectively, and F_ext is an extra interference force; in the method, x(t) can be obtained according to a surface electromyographic signal and joint angle relationship model, and $\dot{x}$(t) and $\ddot{x}$(t) are a first-order derivative and a second-order derivative of x(t), respectively; and K can be obtained according to the model of the surface electromyographic signal to the human stiffness, a relationship between the damping coefficient and the spring (stiffness) coefficient of the system is $B=2\sqrt{K}$, the object mass Mis a mass of a target preset in a training game, and the extra interference force F_ext is a variable virtual force set in the training game.

4. A method for using the wrist rehabilitation training system based on muscle coordination and variable stiffness impedance control according to claim 1, comprising: firstly, collecting and preprocessing surface electromyographic signals during flexion and extension of wrists and fingers of dominant limbs of a patient, then determining a surface electromyographic signal and joint angle relationship model and a surface electromyographic signal and human stiffness relationship model through a muscle coordination method, then setting game scene and difficulty, then collecting and preprocessing surface electromyographic signals of non-dominant limbs of the patient, then obtaining a joint angle and human stiffness according to the surface electromyographic signal and joint angle relationship model and the surface electromyographic signal and human stiffness relationship model, and finally, controlling an agent in a virtual environment to complete a rehabilitation training task through a variable stiffness impedance control method.

* * * * *